(12) United States Patent
Jonsson et al.

(10) Patent No.: US 9,085,547 B2
(45) Date of Patent: Jul. 21, 2015

(54) PROCESS FOR AUTOCATALYTIC ESTERIFICATION OF FATTY ACIDS

(75) Inventors: Susanne Jonsson, Linköping (SE); Bent Sarup, Fredensborg (DK)

(73) Assignee: ALFA LAVAL CORPORATE AB, Lund (SE)

( * ) Notice: Subject to any disclaimer, the term of this patent is extended or adjusted under 35 U.S.C. 154(b) by 0 days.

(21) Appl. No.: 14/111,398

(22) PCT Filed: Apr. 12, 2012

(86) PCT No.: PCT/EP2012/056630
§ 371 (c)(1),
(2), (4) Date: Oct. 11, 2013

(87) PCT Pub. No.: WO2012/140111
PCT Pub. Date: Oct. 18, 2012

(65) Prior Publication Data
US 2014/0039206 A1    Feb. 6, 2014

(30) Foreign Application Priority Data
Apr. 14, 2011 (SE) .................................. 1100281

(51) Int. Cl.
*C07D 311/00* (2006.01)
*C07D 311/58* (2006.01)
(Continued)

(52) U.S. Cl.
CPC ............... *C07D 311/58* (2013.01); *C10G 3/42* (2013.01); *C11B 13/00* (2013.01); *C11C 1/10* (2013.01);
(Continued)

(58) Field of Classification Search
CPC ............. C11C 3/02; C11C 3/10; C11C 3/06; C11C 3/003; C11C 1/10; C11B 13/00; Y02E 50/13; C07D 311/58; C10G 3/42

USPC .................................................. 549/408, 413
See application file for complete search history.

(56) References Cited

U.S. PATENT DOCUMENTS 5,424,457 A    6/1995    Sumner, Jr. et al.
5,627,289 A    5/1997    Jeromin et al.
(Continued)

FOREIGN PATENT DOCUMENTS

CN    1465262 A    1/2004
CN    101173176 A    5/2008
(Continued)

OTHER PUBLICATIONS

Gunawan et al., "Vegetable Oil Deodorizer Distillate: Characterization, Utilization and Analysis", Separation & Purification Reviews, 38: 2009, pp. 207-241.
(Continued)

*Primary Examiner* — T. Victor Oh
(74) *Attorney, Agent, or Firm* — Birch Stewart Kolasch & Birch, LLP

(57) ABSTRACT

The present invention relates to a process for isolation of micronutrients from deodorizer distillate comprising free fatty acids, the process comprises the following steps: (i) treating the deodorizer distillate in an esterification step with glycerol, which esterification step is autocatalyzed, producing a feedstock of acyl glycerides, and discharging excess of glycerol and produced water; (ii) transferring the feedstock of acyl glycerides having a water content less than 1500 ppm and a free fatty acid content less than 3 wt % to a transesterification step and treating the feedstock of acyl glycerides with methanol to produce a crude biodiesel product; and (iii) refining the crude biodiesel product in a distillation step, and separating the crude biodiesel product into three fractions 1) fatty acid methyl esters, 2) micronutrient rich product comprising tocopherol, and 3) light hydrocarbons.

15 Claims, 3 Drawing Sheets

(51) Int. Cl.

| | |
|---|---|
| *C11C 3/02* | (2006.01) |
| *C11C 3/10* | (2006.01) |
| *C11B 13/00* | (2006.01) |
| *C11C 1/10* | (2006.01) |
| *C11C 3/00* | (2006.01) |
| *C11C 3/06* | (2006.01) |
| *C10G 3/00* | (2006.01) |

(52) U.S. Cl.
CPC . *C11C 3/003* (2013.01); *C11C 3/02* (2013.01); *C11C 3/06* (2013.01); *C11C 3/10* (2013.01); *Y02E 50/13* (2013.01)

(56) References Cited

U.S. PATENT DOCUMENTS

| | | |
|---|---|---|
| 6,750,359 B1 | 6/2004 | Copeland et al. |
| 7,368,583 B2 | 5/2008 | Czuppon et al. |

FOREIGN PATENT DOCUMENTS

| | | |
|---|---|---|
| EP | 2 028 260 A1 | 2/2009 |
| GB | 2 451 580 A | 2/2009 |
| JP | 57016878 A | 1/1982 |
| JP | 8-500598 A | 1/1996 |
| JP | 2007-502271 A | 2/2007 |
| WO | WO 2005/019153 A1 | 3/2005 |
| WO | WO 2008/007231 A1 | 1/2008 |
| WO | WO 2008/125574 A1 | 10/2008 |

OTHER PUBLICATIONS

International Search Report, issued in PCT/EP2012/056630, dated Aug. 13, 2012.

Pete Faessler, "Recent Developments and Improvements in Palm Oil Stripping and Fatty Acid Distillation", Sulzer Chemtech Singapore, Feb. 17, 1998, pp. 1-13.

Written Opinion of the International Searching Authority, issued in PCT/EP2012/056630, dated Aug. 13, 2012.

English translation of Chinese Office Action and Search Report, issued Jun. 19, 2014, for Chinese Application No. 201280017871.3.

Qingmei et al., "Deacidification of high-acid rice bran oil by esterification for the raw material of biodiesel", Transactions of the CSAE, vol. 25, No. 8, Aug. 2009, pp. 215-219.

PROCESS FOR AUTOCATALYTIC ESTERIFICATION OF FATTY ACIDS

The present invention relates to a process for isolation of micronutrient and biodiesel from an oil rich in free fatty acids.

BACKGROUND OF THE INVENTION

Most edible oils go through a refining operation of which the last processing step is deodorization where a by-product or distillate with Free Fatty Acids, i.e. FFA, is produced. Besides the FFA's the distillate also contains valuable components such as tocopherols and tocotrienols, i.e. vitamin E and antioxidants, other components are sterols and squalene, these components are mentioned as a group often known as micronutrients.

A current trend in the edible oil industry is to use certain enzymes. A suitable enzyme is phospholipase A to enable removal of phosphor containing components of the crude edible oil down to very low concentration, i.e. ppm levels. However, a side effect of this process will increase production of FFA, which increase will dilute the micronutrients in the deodorizer distillates even more.

In recent years some refiners have in their deodorization sections included a condensation zone at high temperature in known as double scrubbers. Double scrubbers are disclosed for example in U.S. Pat. No. 6,750,359. Double scrubbers could be used to withdraw a process stream enriched in micronutrients. However, use of a double scrubber arrangement may lead to significant loss of micronutrients in the FFA rich overhead stream. A significant limitation of such an approach is that the separation efficiency is linked to the operating conditions of the deodorizer, where the main function is to produce edible oil by of stripping by steam under vacuum.

Esterification of fatty acids with methanol to produce fatty acid methyl esters is known, and is most often practiced in industry in multiple steps using a strong acid, such as sulphuric acid as catalyst. One disadvantage of any methanol esterification is the equilibrium conversion limitation, overcome only by removing water produced by the reaction, but thereby also simultaneously removing methanol, which has to be recovered.

Using glycerol instead of methanol for the esterification, the FFA is transferred to glycerides instead of methylesters. Glycerol esterification of FFA has been described using different types of catalysts, such as ZnO or $ZnCl_2$, or enzymatic or solid phase catalysts. Using a catalyst will impose capital and operating costs, as well as adding effluent streams, unacceptable for large-scale commercial production. Zink, for example is considered environmental toxic for aquatic organisms. Enzymatic glycerol esterification is disclosed by WO 2008/125574.

Processes to purify micronutrients may involve a number of processing steps such as vacuum distillation, esterfications, transesterfications, saponification, short path distillation, e.g. as disclosed in U.S. Pat. No. 7,368,583. Common for such process is that it is much preferred to have as feed stream to the processes a concentrated stream of micronutrients to decrease the size of the purification plant, increase the yield of micronutrients, but also to lower the cost of transportation bringing the feed stream to the purification facility.

One problem with vacuum distillation methods for concentration of tocopherol concentrates according to the known methods are the significant loss of tocopherols and sterols with the produced FFA rich distillate. One of the reasons for the loss of tocopherols, when removing free fatty acids from tocopherols, is their similar vapour pressures. Also, storage and further refining of tocopherols require special precautions since tocopherols are readily oxidized.

Accordingly, there is a clear need for a more specified process that allows micronutrients to be refined to higher extent.

OBJECTS OF THE INVENTION

Accordingly, the present invention provides solutions to the above mentioned problems. The following objects of the invention are:
- transforming oils rich in micronutrients to methylesters and thereby facilitate separation of the micronutrients from the bulk stream,
- combining production of a more valuable micronutrient stream by simultaneous production of biodiesel from the methylesters.
- utilizing fatty raw materials with high free fatty acid content for the production of acylglycerides by esterification using glycerol without utilization of an externally added catalyst.
- providing an esterification process that can accommodate a wide range of raw materials with varying free fatty acid contents.
- eliminate water in the feed used for production of methylesters, which otherwise require drying facilities of the methanol.

These and further objects of the invention will become apparent from the description and the examples hereinafter.

SUMMARY OF THE INVENTION

The present invention provides a solution the problem of loss of tocopherols and sterols with the FFA rich distillate by the new process for isolation of micronutrients and biodiesel. According to the new process is it possible to provide enrichment of micronutrients from deodorizer distillate. The present invention relates to process for isolation of micronutrients from deodorizer distillate comprising free fatty acids. The process comprises the following steps:
(i) treating the deodorizer distillate in an esterification step with glycerol, which esterification step is autocatalysed, producing a feedstock of acyl glycerides, and discharging excess of glycerol and produced water;
(ii) transferring the feedstock of acyl glycerides having a water content less than 1500 ppm and a free fatty acid content less than 3 wt % from esterification step (i) to a transesterification step and treating the feedstock of acyl glycerides with methanol to produce a crude biodiesel product; and
(iii) refining the crude biodiesel product in a distillation step, and separating the crude biodiesel product into three fractions 1) fatty acid methyl esters, 2) micronutrient rich product comprising tocopherol, and 3) light hydrocarbons.

DETAILED DESCRIPTION OF THE INVENTION

The process for isolation of micronutrients and biodiesel from a FFA rich stream of the invention comprises the above mentioned steps, i.e.
- esterification step (i);
- transesterification step (ii); and
- distillation step (iii).

Esterification step (i) comprises esterification of the deodorizer distillate. The esterification is performed with glycerol producing a feedstock of acyl glycerides. The process comprises also discharging produced water by means of a vacuum system. Fortunately, it was found that that by optimizing the esterification reaction conditions within a feasible residence time, the fatty acids could be converted to a sufficiently low level without adding a catalyst or without adding an enzyme, and thus rely on the inherent autocatalytic capability of the fatty acids. All mentioned wt % is percent by weight.

Transesterification step (ii) comprises transferring the dry feedstock blend to a transesterification step, and treating the feedstock with methanol. According to an alternative may an alkaline catalyst be used for treating the feedstock to produce a crude biodiesel.

Distillation step (iii) comprises refining the crude biodiesel product by distillation and separating the crude biodiesel product into three fractions.

Before the deodorizer distillate is entering esterification step (i) the deodorizer distillate may be deaerated under vacuum within the range from about 2 to about 50 mbar according to one alternative of the process. According to another alternative the deodorizer distillate may be deaerated under vacuum within the range from about 5 to about 30 mbar.

According to another alternative the deodorizer distillate may be pre-heated before entering esterification step (i). The pre-heating may be to a temperature within the range from about 50 to about 90° C. According another alternative may the process comprise that the deodorizer distillate may be pre-heated to a temperature within the range from about 60 to about 70° C. before entering the esterification step.

According to the process of the invention, the esterification in the esterification step (i) the initial mass ratio deodorizer distillate to glycerol was less than 5:4. According to another alternative the initial mass ratio to glycerol in esterification step (i) may be within a range from about 5:1 to about 5:4. According to another alternative the initial mass ratio deodorizer distillate to glycerol may be within a range from about 4:1 to about 4:3. According to a further alternative the initial mass ratio deodorizer distillate to glycerol may be within the range from about 10:3 to about 10:7.

According to an alternative of the process of the invention, the deodorizer distillate in the esterification step (i) may have an initial content of the free fatty acids within a range from about above 10 wt % to about 100 wt % free fatty acids.

According to an alternative of the process of the invention esterification step (i) may comprise providing an esterified product having a content of less than 3 wt % FFA. Suitably a target value for the FFA according to one alternative for the transesterification step would be to have a target value of less than 1.5 wt %. According to another alternative a value for the FFA from the glycerol esterification step would suitable be within the range from about 0.2 to about 1.2 wt % FFA. Suitable, the pre-treated oil will have a maximum of free fatty acid content of 0.8 wt %. According to a further alternative the target value may be within the range from about 0.5 to about 0.8 wt % FFA. The loss of tocopherols over the esterification line will suitably not exceed 1 wt % of the tocopherols in the raw oil/fat for the esterification line.

According to an alternative of the process of the invention esterification step (i) may be carried out under vacuum within the range from about 2 to about 500 mbar. According to another alternative of the invention the esterification may be carried out under vacuum within the range from about 10 to about 300 mbar. According to further alternative of the invention the esterification may be carried out under vacuum within the range from about 40 to about 130 mbar.

According to an alternative of the process of the invention esterification step (i) may also comprise reduction of pressure during the final esterification time. According to another alternative the reduction of pressure in esterification step (i) may be within the range from about 100 to about 20 mbar. According to further alternative the reduction of pressure in esterification step (i) may be within the range from about 100 to about 30 mbar. According to further alternative the reduction of pressure in esterification step (i) may be within the range from about 80 to about 50 mbar.

According to an alternative of the process of the invention esterification step (i) may also comprise reduction of pressure may be performed during the final 60 minutes of the esterification. According to another alternative the reduction of pressure may be performed during the final 40 min According to further alternative the reduction of pressure may be performed during the final 20 minutes of the esterification step (i).

According to an alternative of the process of the invention esterification step (i) the esterification may be carried out at a temperature within a range from about 140 to about 200° C. According to another alternative of the invention the esterification may be carried out at temperatures within a range from about 180 to about 200° C.

According to an alternative of the process of the invention esterification step (i) may comprise adding pre-treated oils to the feedstock blend of acyl glycerides.

According to an alternative of the process of the invention esterification step (i) the feedstock of acyl glycerides may have a water content less than 500 ppm when transferred to the transesterification step. According to another alternative the feedstock of acyl glycerides may have a water content less than 400 ppm when transferred to the transesterification step According to another alternative the feedstock of acyl glycerides may have a water content less than 300 ppm when transferred to the transesterification step.

According to an alternative of the process of the invention transesterification step (ii) may comprise addition of an alkaline catalyst to produce a crude biodiesel product.

The process according to the invention may comprise that transesterification step (ii) comprises release of glycerol. The released glycerol may be pre-treated and used in the esterification step (i). The pre-treatment may comprises methanol evaporation and neutralization, if an alkaline catalyst was used, followed by separation of the formed salt.

According to an alternative of the process of the invention distillation step (iii) may be carried out at a temperature within a temperature range from about 130 to about 280° C. According to another alternative distillation step (iii) may be carried out at a temperature within a temperature range from about from about 200 to about 270° C. According to a further alternative distillation step (iii) may be carried out at a temperature within a temperature range from about from about 220 to about 270° C. According an alternative of the invention may the process comprise that the distillation in the distillation step may be carried out under a suction pressure within a range from about 0.001 to about 7 mbar in a vacuum system. According another alternative may the process comprise that the distillation step (iii) is carried under a suction pressure within a range from about 0.5 to about 4 mbar in a vacuum system. According a further alternative may the process comprise that the distillation step (iii) is carried under a suction pressure within a range from about 1.5 to about 3 mbar in a vacuum system.

According an alternative of the invention may the process comprise that the distillation in the distillation step may be carried out at a temperature within a temperature range from about 130 to about 280° C., and under a suction pressure within a range from about 0.001 to about 7 mbar. According to another alternative the distillation step may be carried out at a temperature within a temperature range from about from about 220 to about 260° C. and a suction pressure from about 1.5 to about 3 mbar, in a vacuum system.

The present invention comprises a way of converting FFA to acylglycerides prior transesterification to biodiesel. By using glycerol instead of methanol for the esterification in esterification step (i) enables water removal without significant removal of the alcohol due to the large disparity of vapour pressure between water and glycerol. In this way, the conversion limitation imposed by thermodynamics can be overcome. Also the final product from esterification step (i) may be considered as dry and therefore, subsequent methanol transesterification to methylesters may be possible without any pretreatment. Additionally, the methanol recovered from the transesterification, can be recovered and reused without any drying procedure. One advantage of the invented method which comprises glycerol esterification in conjunction with methanol transesterification and distillation is to use glycerol to esterify fatty acids and to allow removal of water without removing the alcohol as would be the case if methanol was used as practiced in conventional esterification in biodiesel manufacture. The water removal is required to achieve high conversion levels of fatty acids since a higher equilibrium conversion can be obtained at lower water activity levels. At the same time, the alcohol, i.e. glycerol, is a necessary reactant, and a high concentration promotes both the reaction rate as well as a high equilibrium conversion.

Surprisingly it has been found that that by optimizing the reaction conditions within a feasible residence time the fatty acids could be converted to a sufficiently low level without adding a catalyst, and thus rely on the autocatalytic capability of the fatty acids.

Thus the present invention provides a process for glycerol esterification, and using this glycerol esterification process to provide a surprisingly high economical benefit for the production of micronutrients.

To circumvent this it is advantageous to convert the fatty acids to their corresponding methyl esters Fatty Acid Methyl Esters (FAME) which has a significantly higher vapour pressure than their corresponding fatty acids. This facilitates their separation by vacuum distillation, meaning that the yield of tocopherols and other valuable micronutrients can be maximized while using a relatively low temperature at vacuum levels that are economical to establish.

Biodiesel processes have problems with treatment of oils with FFA content higher than 8 wt %. Therefore, for oils with a content within the range from about 8 to 100 wt % FFA it may be necessary to have pre-treatment of the oils to reduce the FFA and convert them into glycerides, which can be further converted into biodiesel in the transesterification process.

Yet a further advantage would be that the processing severity during glycerol esterification is relatively low, i.e. maximum 200° C., which could reduce the formation of undesirable by-products, such as acrolein and diglycerol.

By transforming FFA to their methyl esters facilitates separation of the micronutrient rich product stream by relatively mild and economically feasible vacuum distillation.

By removing micronutrients from the product stream generated from the transesterification gives both the advantage of forming a high value product, rich in micronutrients, and also provides a high purity fatty acid methyl ester stream, which otherwise would have too high content of "unsaponifiable" to adhere to biodiesel norms such as EN14214.

The enriched tocopherol product from this process, has high quality and high value and an even higher value than the biodiesel product. Thus the new process benefits by producing two products which could be used in different applications.

In the following the present invention is described by the aid of figures and examples, which are for the purpose of explaining the invention and should not limit the scope of invention.

DETAILED DESCRIPTION OF THE DRAWINGS

Figure 1:
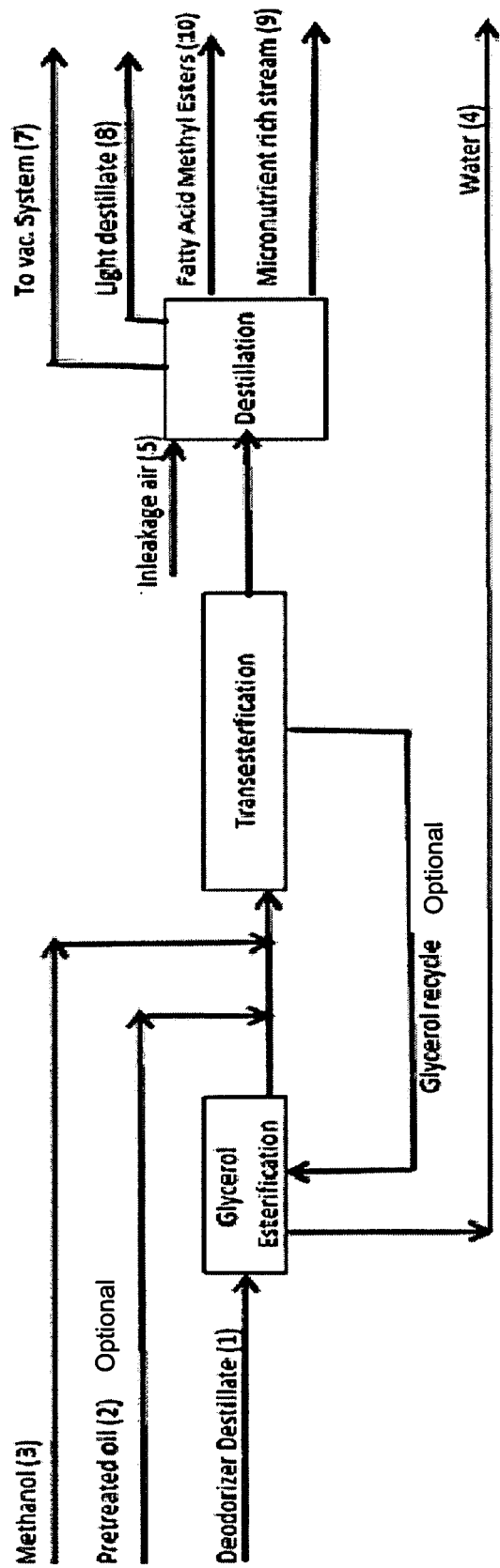
FIG. 1 shows the overall process according to the invention.

In FIG. 1 a process for isolation of biodiesel and micronutrient is shown. According to FIG. 1 the free fatty acids (FFA) in a deodorizer distillate 1 react with recycled glycerol in a glycerol esterification step (i). The free fatty acids are converted by the glycerol to a feedstock of acyl glycerides. Water 4 is formed as a byproduct of the esterification reaction in this step, the water is lead out of the system in step (i). The output stream from the glycerol esterification step may be suitable as a feedstock of acyl glycerides for a transesterification step (ii) without any additional pre-treated oil. According to another alternative the output stream from the glycerol esterification step (i) could be combined with a stream of pre-treated oil 2 to form a feed stock blend together the feedstock of acyl glycerides, which is suitable for a transesterification step (ii). The feedstock stream is treated with methanol 3 and an optionally alkaline catalyst in the transesterification step to produce a crude biodiesel product. Released glycerol may, if pre-treated, be used in the esterification step (i). The pre-treatment comprises methanol evaporation and neutralization, if an alkaline catalyst was used, followed by separation of the formed salt. The crude biodiesel product from the transesterification step is then refined in a distillation step (iii), i.e. a vacuum distillation tower. In the distillation step the crude biodiesel fraction is separated by distillation into one stream of fatty acid methyl esters (FAME), i.e. biodiesel 10, a stream of micronutrient rich product 9, and a stream of light hydrocarbons 8. Inleakage or inlets of air 5 to the distillation step will give a stream of non-condensables 7 going to a vacuum system for further processing. An example of the overall mass balance for the process according to this embodiment is summarised in Table 1.

TABLE 1

| | Stream Nr. | | | | | | | | | |
|---|---|---|---|---|---|---|---|---|---|---|
| | 1 | 2 | 3 | 4 | 5 | 6 | 7 | 8 | 9 | 10 |
| | Flow kg/hr | | | | | | | | | |
| | 3687.5 | 3687.5 | 688.4 | 128.1 | 10.0 | 494.3 | 43.2 | 64.0 | 1600.0 | 5743.8 |
| TAG | 2.0000 | 95.5975 | 0.0000 | 0.0000 | 0.0000 | 0.0325 | 0.0000 | 0.0000 | 2.3582 | 0.0000 |
| DAG | 8.0000 | 2.0000 | 0.0000 | 0.0000 | 0.0000 | 0.0069 | 0.0000 | 0.0000 | 0.5043 | 0.0000 |
| MAG | 4.0000 | 0.9500 | 0.0000 | 0.0000 | 0.0000 | 0.0166 | 0.0000 | 0.0000 | 1.2009 | 0.0000 |

TABLE 1-continued

| | Stream Nr. | | | | | | | | | |
|---|---|---|---|---|---|---|---|---|---|---|
| | 1 | 2 | 3 | 4 | 5 | 6 | 7 | 8 | 9 | 10 |
| | Flow kg/hr | | | | | | | | | |
| | 3687.5 | 3687.5 | 688.4 | 128.1 | 10.0 | 494.3 | 43.2 | 64.0 | 1600.0 | 5743.8 |
| FFA | 55.0000 | 0.6000 | 0.0000 | 0.0000 | 0.0000 | 0.0432 | 0.0000 | 0.0000 | 2.1562 | 0.2721 |
| TOCO's | 13.5000 | 0.0500 | 0.0000 | 0.0000 | 0.0000 | 0.4286 | 0.0000 | 0.0000 | 31.0969 | 0.0000 |
| STEROLS | 12.5000 | 0.8000 | 0.0000 | 0.0000 | 0.0000 | 0.4207 | 0.0000 | 0.0000 | 30.5231 | 0.0000 |
| SQUALNE | 2.0000 | 0.0025 | 0.0000 | 0.0000 | 0.0000 | 0.0633 | 0.0000 | 0.0000 | 4.5957 | 0.0000 |
| LIGHT HC'S | 3.0000 | 0.0000 | 0.0000 | 0.0000 | 0.0000 | 0.0094 | 75.0453 | 99.6060 | 0.0000 | 0.2505 |
| GLYCEROL | 0.0000 | 0.0000 | 0.0000 | 0.0084 | 0.0000 | 96.1263 | 0.0000 | 0.0007 | 0.0003 | 0.0196 |
| WATER | 0.0000 | 0.0000 | 0.1000 | 99.9916 | 0.0000 | 0.1689 | 0.0044 | 0.0001 | 0.0000 | 0.0000 |
| AIR | 0.0000 | 0.0000 | 0.0000 | 0.0000 | 100.0000 | 0.0000 | 23.1664 | 0.0001 | 0.0000 | 0.0000 |
| METHYLESTERS | 0.0000 | 0.0000 | 0.0000 | 0.0000 | 0.0000 | 0.5253 | 0.0000 | 0.3751 | 27.5644 | 99.4578 |
| METHANOL | 0.0000 | 0.0000 | 99.9000 | 0.0000 | 0.0000 | 2.1583 | 1.7839 | 0.0179 | 0.0000 | 0.0000 |

Figure 2:
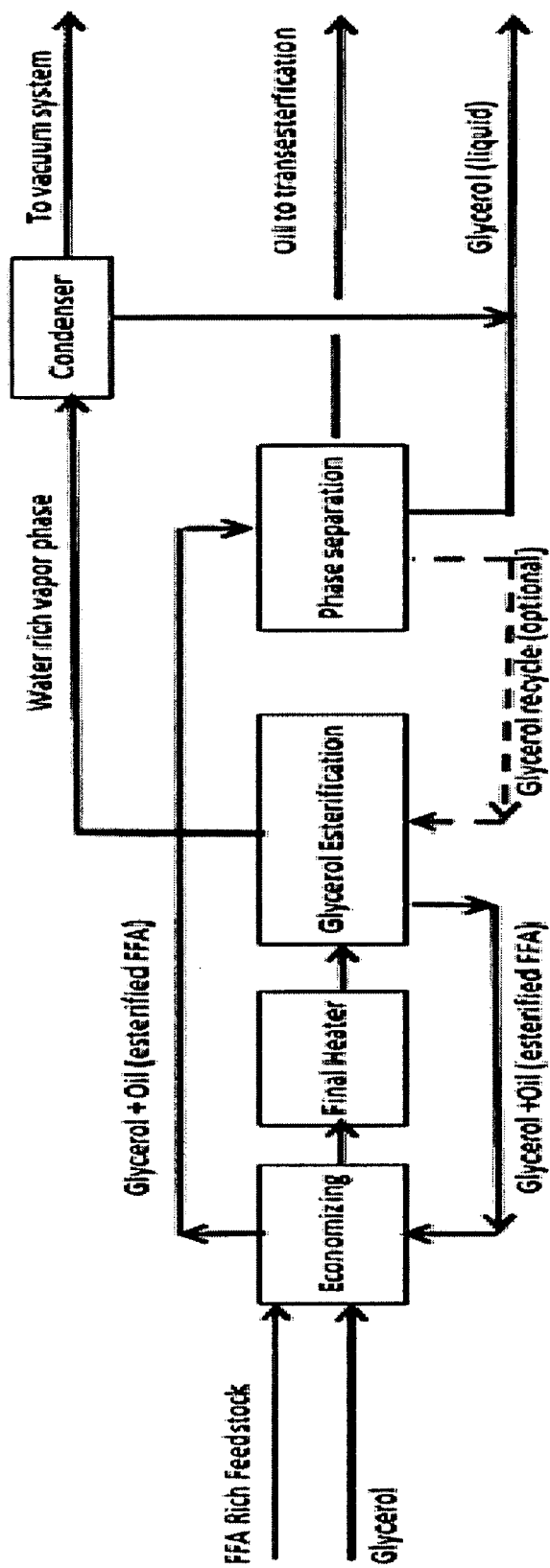
FIG. 2 shows the glycerol esterification step according to the invention.

FIG. 2 shows the glycerol esterification step. In the glycerol esterification step a FFA rich feedstock and glycerol are combined to form a feedstock blend. The feedstock blend is then economized to utilize sensitive heat from effluents coming from the glycerol esterfication reactor. In a final heater the feedstock blend brought to reaction temperatures. According to an alternative the reaction temperatures may be lower at the beginning of the reaction and higher at the end. By this, both deterioration of the micronutrients and co-evaporation of glycerol are minimized.

By the glycerol esterification, which could be reversible, the FFA reacts with glycerol and form a mixture of water and of tri-, di- and monoacylglycerides. These glycerides are often abbreviated as TAG, DAG, MAG. The product from the glycerol esterification step (i), i.e. the feedstock blend of acyl glycerides, is suitable transferred as feedstock to the downstream transesterification step (ii). The esterification reaction is suitably conducted under vacuum. Vacuum allows water and other volatiles, such as inleakage or inlets of air which otherwise could deteriorate the micronutrients, to escape the reaction environment, and thus improve the achievable equilibrium conversion by a product removal. In the vapour stream from the reactor there will be some co-evaporated glycerol. According to one embodiment of the invention may a condensation stage be included to preferentially condense the glycerol, and recover this glycerol rather than having the glycerol escape to the vacuum system to end up in effluents from the plant.

The reaction proceeds in the absence of an external catalyst, i.e. as an autocatalytic reaction where the Brönsted acidity of the fatty acids serves as catalyst.

After economizing with the incoming feed, the reactor effluents enter a liquid-liquid separation stage, separating the produced oil from the glycerol phase. Optionally, part of the glycerol can be recycled to the glycerol esterification stage, for example if this could increase the reuse of a catalyst preferentially soluble in the glycerol phase.

The glycerol esterification process comprises that homogenized, pre-heated feedstock having a temperature within the range from about 70 to about 90° C. enters the plant via a feed tank or from storage. The feed oil is pumped at the desired flow rate by a feed pump through a screen filter. Glycerol is injected at a controlled rate by means of one or two pumps. The mixture is intensively contacted with the oil in a mixer or blender. The mixture is then heated to a temperature around about 160° C. in one or two economizers before being flashed trough spray nozzles into at least one reactor.

In the reactors, the mixture is circulated by means of pumps over the heat exchangers, where the mixture may be heated by thermal oil to reaction temperature within the range from 140 to about 200° C. According to an alternative the mixture may be heated within the range from about 160 to about 200° C. According to another alternative the mixture may be heated within the range from about 160 to about 200° C.

During the reaction, FFA:s are converted into glycerides:

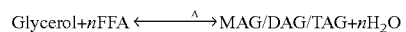

$$\text{Glycerol} + n\text{FFA} \xleftrightarrow{\Delta} \text{MAG/DAG/TAG} + n\text{H}_2\text{O}$$

Conversion of free fatty acids (FFA) to monoglycerides (MAG), diglycerides (DAG) and triglycerides (TAG) is carried out by using glycerol in presence of heat and resulting in production of water ($H_2O$). The produced water is sucked by mean of vacuum systems. The vacuum systems comprise a condenser, a vapour/liquid separator, a vacuum pump and a waste water pump. The reactors for the conversion could be carried out in a tank reactor equipped with agitators in order to accelerate the esterification process by increasing the number of liquid droplets and thereby increasing the contact area of reagents, but other types of reactors such as plate reactors and tube reactors are also possible. The reaction could be batch wise, but a continuous reaction is also possible. In case of a continuous reaction then the reaction is carried out in a plate reactor or in a tube reactor.

After a predefined reaction time, the batch or the feedstock may be pumped from the reactor to a drop tank. From the drop tank, a pump can transfer the feedstock through the economizers, where the reacted oil is cooled down while heating the feed oil. The cooled feedstock can be transferred into a settling tank.

The top phase of the feedstock, containing the esterified oil, may be transferred by a pump to a storage tank.

The excess glycerol may be discharged from the bottom of the settling tank and transferred by a pump to the glycerol storage tank. The settling tank may be equipped with phase separation sensors to enable adequate volume extractions of the different phases from the tank. The discharged glycerol may be reused in the esterification process (i).

EXAMPLES

For the examples given below, 1200 g of existing oil distillates were used in each experiment. The distillates comprised of 1 to 6 wt % tocopherols. The glycerol, originating from a biodiesel plant using methanol and sodium methylate for transesterification of rapeseed oil, was a neutralized and separated from formed FFA and precipitated salts. The specification of the glycerol was 92 wt % glycerol, 3 wt % water, 4 wt % methylesters (biodiesel) and 1 wt % FFA.

Example 1

In this example, three tests with oil distillates containing 21, 60 and 87 wt % FFA were mixed with glycerol in a mass ratio of 2:1. The mixture was introduced into a stirred reactor held at a pressure of 100 mbar and at a temperature of 200° C. Samples were withdrawn frequently for measurements of the acid value. After 6 hours reaction, the FFA content in the 20, 60 and 90 wt % oils had been reduced to 1.5, 1.0 and 0.7 wt %, respectively due to formation of mono-, di- and triacylglycerides.

This example shows that the esterification of FFA and glycerol is autocatalyzed and is capable of reducing FFA in oils, covering a wide span of initial FFA concentrations, within a reasonable period of time.

Example 2

In this example, the effect of the pressure was investigated in three separate tests. Palm oil fatty acid distillate containing 86 wt % FFA and glycerol were used at a mass ratio of 4:3. The reaction temperature was 200° C. and the pressure during the reaction time was 400, 200 and 100 mbar. After 6 hours, the FFA content was 4.1, 1.5 and 0.2 wt %, respectively.

This example shows that it is possible to reduce the final FFA by reducing the pressure in the reaction vessel.

Example 3

In this example, the temperature was investigated in three separate tests. The same palm oil fatty acid distillate and glycerol as in example 2 was used and the mass ratio was 2:1. The reaction pressure was set to 100 mbar and the reaction temperature was isocratic at 160, 180 and 200° C. After 6 hours, the FFA content in each test was 19.3, 4.3, and 0.6 wt %, respectively.

This example shows that increased temperature generates lower final FFA contents.

Example 4

In this example, the mass ratio of oil:glycerol was investigated. The same palm oil fatty acid distillate as in example 2 was used and the reaction temperature and pressure was 200° C. resp. 100 mbar. The oil:glycerol mass ratios were 4:1, 2:1 and 4:3. After 6 hours, the FFA content was 1.7, 0.6 and 0.15 wt %, respectively.

This example shows that higher oil/glycerol ratios favor the autocatalytic esterification, generating lower final FFA concentrations.

Example 5

In this example, a temperature ramp 170 to 200° C. was applied during the first 3 hours, whereafter the temperature was held constant at 200° C. the following 3 hours. The pressure was 100 mbar. After 6 hours, the content of FFA was 1.1 wt %. A FFA content of 0.4 wt % was observed after 6 h 40 min.

Figure 3:
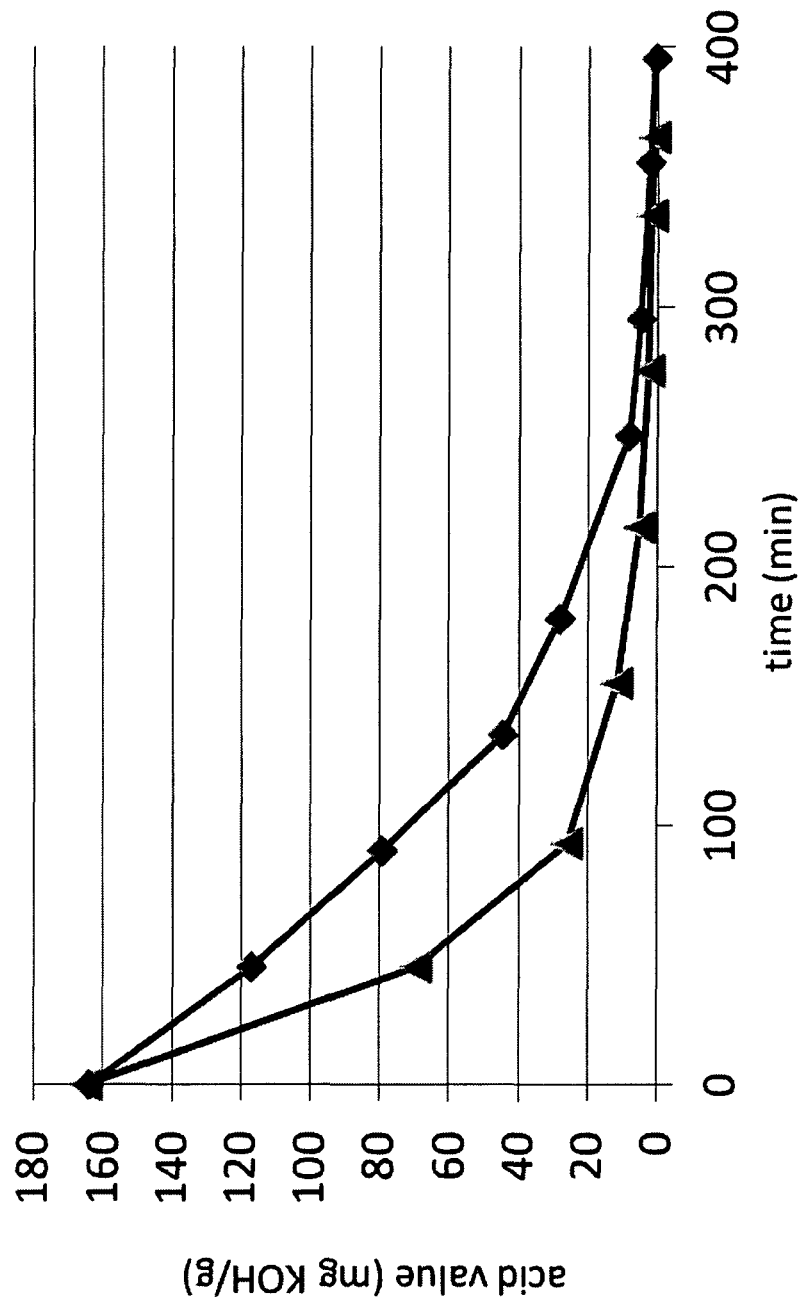
FIG. 3 shows a diagram which is a result of the tests in Example 5.

This example shows that initial temperature programming can reach about the same final acid value as the isocratic esterification at 200° C. with the same timeframe, even though the initial esterification rate is slower than for the isocratic, see FIG. 3. The diagram of FIG. 3 shows a temperature programmed esterification ramping 170 to 200° C. during 0 to 180 min followed by constant temperature at 200° C. during 180 to 400 min, in comparison with an isotermic esterification performed at 200° C.

Example 6

In this example, the pressure was reduced from 100 to 50 mbar the final 30 min of the reaction time. Palm oil fatty acid distillate of 87 wt % FFA and glycerol was mixed at a mass ratio of 2:1 at 200° C. Reduction of the pressure reduced the final FFA content about 50 wt %, i.e. from 0.7 to 0.35 wt %.

This example shows that it is possible to polish the final FFA by stripping the last traces of FFA during a short period at the end of the reaction.

Example 7

In this example, the autocatalyzed esterification was studied in conjunction with one catalyzed by zinc oxide. Reaction temperature was 180° C. and vacuum was 100 mbar. The mass ratio of oil:glycerol was 10:3 and the zinc catalyzed experiment was added 0.11 wt % ZnO. The zinc and autocatalyzed esterification reduced the initial FFA concentrations to 0.5 wt % after 4.5 and 9 hours, respectively.

This example shows that the autocatalyzed esterification at 180° C. is only twice as slow as the zinc oxide catalyzed and has the potential to reach acceptable low concentrations of FFA within a reasonable period of time.

Example 8

In this example, 2.5 wt % tocopherols were added to a refined and deodorized glyceride oil. The tocopherol oil was deaerated at 10 mbar for 20 min at 80° C. before adding the glycerol and additional 20 min after addition of the glycerol, before heating to 160, 180 or 200° C. at 100 mbar. β-tocopherol could not be evaluated due to very low initial concentrations. After 8 hours at 200° C., no significant losses of the α-, γ- and δ-tocopherols were observed in any of the experiments.

This example shows that the tocopherols remain intact at the studied temperatures and applied vacuum.

The results of the Examples show that it is possible to eliminate catalyst in esterification step (i) and to produce acyl glycerides by autocatalysis. The results show also that it is possible to reduce the final FFA by the optimizing the esterification reaction conditions.

The invention claimed is:

1. A process for isolation of micronutrients from a deodorizer distillate comprising free fatty acids, wherein the deodorizer distillate is pre-heated to a temperature within a range from about 50 to about 90° C. before entering esterification step (i), the process comprising:
   (i) treating the deodorizer distillate in an esterification step with glycerol, which esterification step is autocatalysed, producing a feedstock of acyl glycerides, and discharging excess of glycerol and produced water;
   (ii) transferring the feedstock of acyl glycerides having a water content less than 1500 ppm and a free fatty acid content less than 3 wt % to a transesterification step and treating the feedstock of acyl glycerides with methanol to produce a crude biodiesel product,
      wherein the transesterification is performed with an alkaline catalyst; and
   (iii) refining the crude biodiesel product in a distillation step, and separating the crude biodiesel product into fractions comprising 1) a fraction comprising fatty acid methyl esters, 2) a fraction comprising micronutrient rich product comprising tocopherol, and 3) a fraction comprising light hydrocarbons.

2. The process according to claim 1, wherein the deodorizer distillate is deaerated under vacuum within a range from about 2 to about 50 mbar before entering esterification step (i).

3. The process according to claim 1, wherein an initial mass ratio of deodorizer distillate to glycerol was less than 5:4.

4. The process according to claim 1, wherein the deodorizer distillate in esterification step (i) has an initial content of the free fatty acids within a range from about above 10 wt % to about 100 wt % free fatty acids.

5. The process according to claim 1, wherein esterification step (i) is carried out under vacuum within a range from about 2 to about 500 mbar.

6. The process according to claim 1, wherein esterification step (i) further comprises reduction of pressure during the final esterification time.

7. The process according to claim 6, wherein the reduction of pressure in esterification step (i) is within a range from about 100 to about 20 mbar.

8. The process according to claim 7, wherein the reduction of pressure in esterification step (i) is performed during a final 60 minutes of the esterification.

9. The process according to claim 1, wherein the esterification in esterification step (i) is carried out at a temperature within a range from about 140 to about 200° C.

10. The process according to claim 1, wherein esterification step (i) further comprises adding pre-treated oils to the feedstock of acyl glycerides.

11. The process according to claim 1, wherein transesterification step (ii) comprises addition of an alkaline catalyst to produce the crude biodiesel product.

12. The process according to claim 1, wherein transesterification step (ii) further comprises release of glycerol, wherein the released glycerol is pre-treated and used in esterification step (i).

13. The process according to claim 1, wherein distillation step (iii) is carried out at a temperature within a temperature range from about 130 to about 280° C.

14. The process according to claim 1, wherein distillation step (iii) is carried under a suction pressure within a range from about 0.001 to about 7 mbar in a vacuum system.

15. A process for isolation of micronutrients from a deodorizer distillate comprising free fatty acids, wherein the deodorizer distillate is pre-heated to a temperature within a range from about 50 to about 90° C. before entering esterification step (i), the process comprising:
(i) esterifying the deodorizer distillate with glycerol, wherein said esterifying step is autocatalysed, and then discharging excess of glycerol and produced water, to produce a feedstock comprising acyl glycerides, wherein the feedstock comprising acyl glycerides has a water content less than 1500 ppm and a free fatty acid content less than 3 wt %;
(ii) transesterifying the acyl glycerides of the feedstock comprising acyl glycerides with methanol to produce a product comprising a crude biodiesel,
wherein the transesterification is performed with an alkaline catalyst; and
(iii) distilling the product comprising the crude biodiesel to separate the crude biodiesel into fractions comprising at least 1) a fraction comprising fatty acid methyl esters, 2) a fraction comprising a micronutrient rich product comprising tocopherol, and 3) a fraction comprising light hydrocarbons.

* * * * *